| United States Patent [19] | [11] Patent Number: 4,929,438 |
| Sawai et al. | [45] Date of Patent: May 29, 1990 |

[54] PREVENTIVES AND REMEDIES FOR MEDICINAL AND ALCOHOLIC POISONING

[75] Inventors: Kiichi Sawai; Masayasu Kurono; Hiromiotu Asai; Takahiko Mitani; Naohisa Ninomiya; Takao Sugiyama; Eiji Furukawa; Hisashi Michishita, all of Nagoya, Japan

[73] Assignee: Kabushiki Kaisha Sanwa Kagaku Kenkyusho, Nagoya, Japan

[21] Appl. No.: 310,162

[22] Filed: Feb. 15, 1989

[30] Foreign Application Priority Data

May 13, 1988 [JP] Japan ............................... 63-116338

[51] Int. Cl.$^5$ ............................................. A61K 27/00
[52] U.S. Cl. ....................................... 424/10; 514/811
[58] Field of Search ........................... 424/10; 514/811

[56] References Cited

PUBLICATIONS

Chem. Abst., vol. 72 (1972), 137820(b).
Vallejo, Mario et al., "Occurrence and Extracellular Actions of Inositol Pentakis- and Hexakisphosphate in Mammalian Brain." *Nature*, vol. 330, No. 6149 (17–23 Dec. 1987), pp. 656–658.

*Primary Examiner*—Stanley J. Friedman
*Attorney, Agent, or Firm*—Armstrong, Nikaido, Marmelstein, Kubovcik & Murray

[57] ABSTRACT

Preventives or remedies for medicinal and alcoholic poisoning contain as a pharmaceutically effective component phytic acid or its salt which may be an innoxious metal salt, or an innoxious salt with an organic base, a basic amino acid or an organic ester residue.

5 Claims, 7 Drawing Sheets

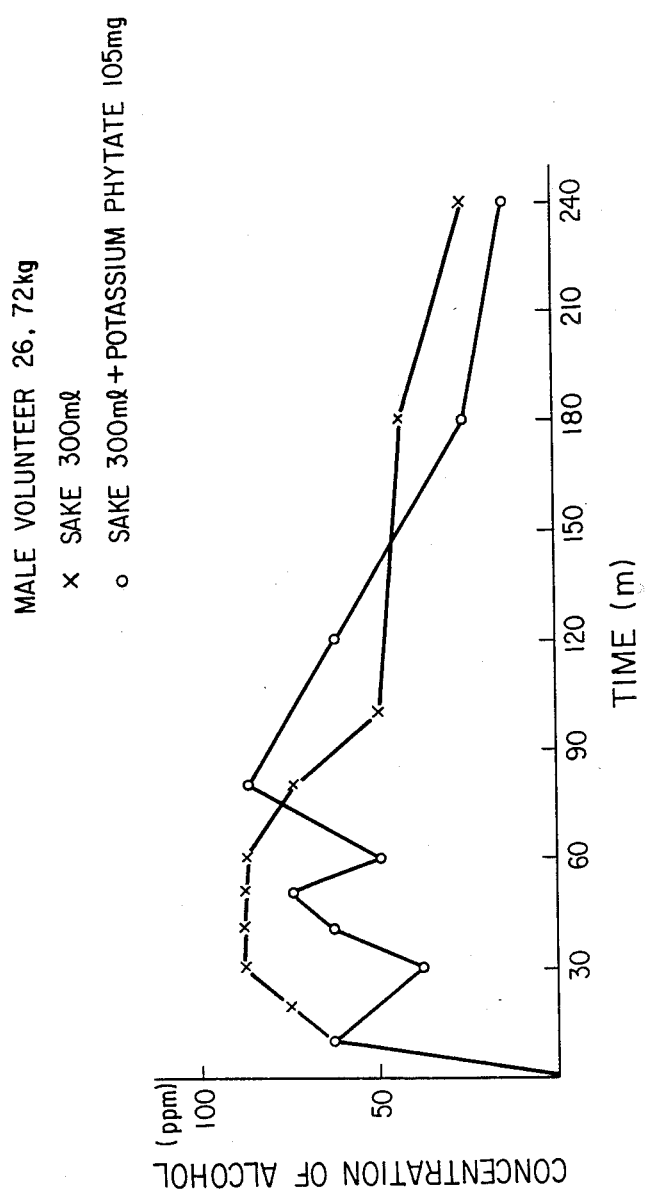

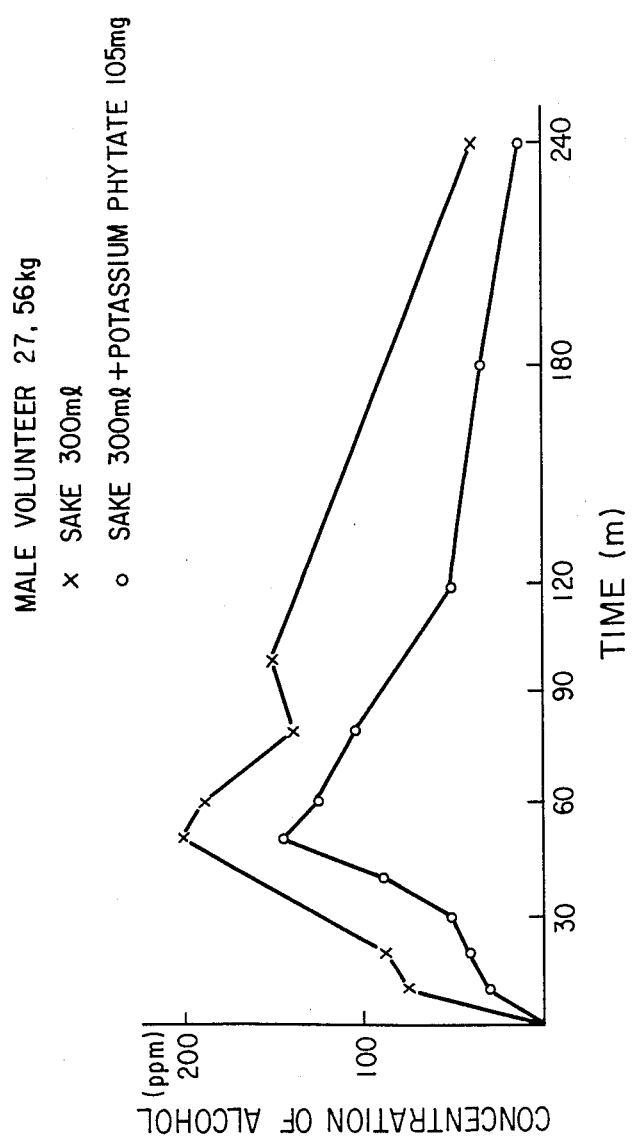

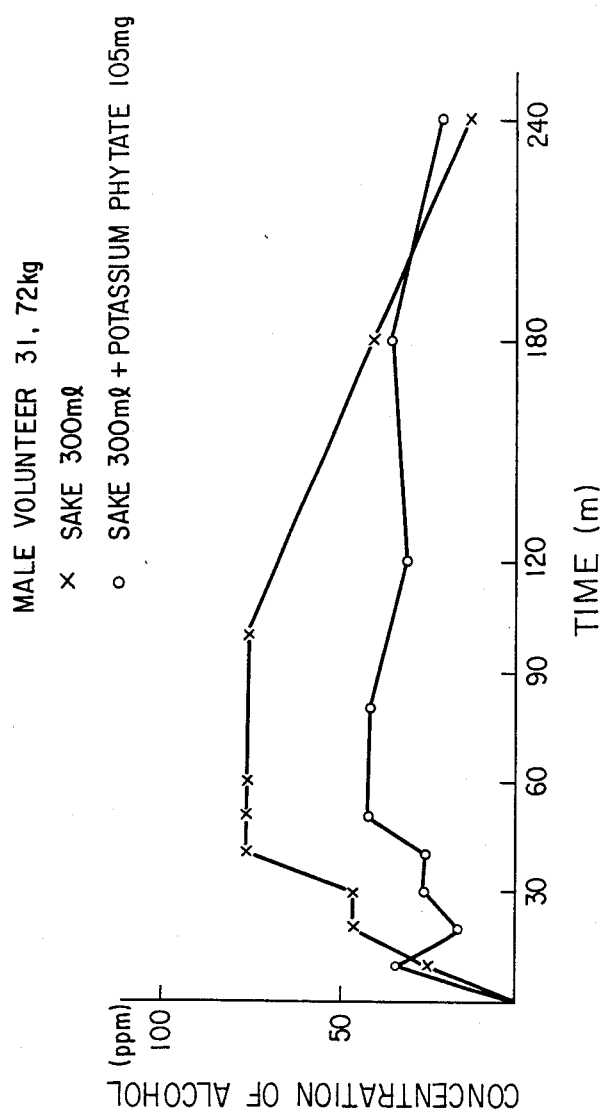

EFFECT OF PHYTIC ACID

2g/kg ORAL ADMINISTRATION OF ETHANOL

——— BEFORE ADMINISTRATION OF PHYTIC ACID

----- AFTER ADMINISTRATION OF PHYTIC ACID

EFFECT OF PHYTIC ACID

2g/kg ORAL ADMINISTRATION OF ETHANOL

——— BEFORE ADMINISTRATION OF PHYTIC ACID

– – – – AFTER ADMINISTRATION OF PHYTIC ACID

PREVENTIVES AND REMEDIES FOR MEDICINAL AND ALCOHOLIC POISONING

BACKGROUND OF THE INVENTION

1. Field of the Invention

The present invention relates to preventives and remedies for medicinal and alcoholic poisoning, which contain phytic acid or its salt as an effective component.

2. Statement of the Prior Art

Therapeutic treatments for poisoning have generally been carried out by e.g., the administration of repellents for the purposes of prohibiting the ingestion of addictive poisioning-inducing substances, the activation of antidotal enzymes by metabolic activation and the chelation and adsorption of toxic substances, and poisoning remedies containing various compounds and pharmaceutically effective components have so far been used for those purposes.

On the other hand, phytic acids widely appear in plants as calcuim and magnesium salts, sometimes a potassium salt. For instance, rice bran contains as high as 9.5 to 14.5% of phytic acid, and provides a starting material for commercial phytic acid and myoinositol deriving therefrom.

Phytic acid and its salt have been used in wide applications; in pharmaceutical applications, calcium phytate has been used as a calcium augmentor, rice bran itself and sodium phytate as a preventive for calcium calculuses, and potassium phytate for the treatment of hypercalcemia and the adjustment of hyper-calciurea of sarcoidosis patients. They have also been utilized in various other fields as fermentative aids for brewing sake and wine, metal removers making use of the chelating action of phytic acid, antioxidants in the presence of iron and calcium ions and anticorrosives for metals.

However, it has not been reported until now that phytic acid and its salts may be used as preventives and remedies for drug poisoning, in particular, acute and chronic alocoholism.

Surprisingly, the inventors have discovered that when orally administered in the process of nutrition experiments, phytic acid serves to reduce body smells, inter alia, foul breath, perspiratory smell and urinous smell. In particular, further studies of the removal of alcoholic breath by phytic acid has revealed that phytic acid takes part in the production and decomposition of alcohols, inter alia, aldehydic substances that are in vivo metabolites and has the property of detoxicating them.

SUMMARY OF THE INVENTION

A primary object of the present invention accomplished on the basis of the aforesaid findings is to provide preventives and remedies for drug poisoning and alcoholism, which contain phytic acid and its salt as an effective component.

The preventives or remedies provided by the present invention are administrable or applicable to both humans and animals.

BRIEF DESCRIPTION OF THE DRAWINGS

The present invention will now be described with reference to the drawings, which are given for the purpose of illustration alone, and in which:

FIGS. 1 to 3 are graphical views illustrating changes-with-time in the concentration of alcohol in breath, as measured in Example 1; FIG. 1 is a graph showing the results of testing with a male volunteer of 26 years old, FIG. 2 a graph showing the results of testing with a male volunteer of 27 years old, and FIG. 3 a graph showing the results of testing with a male volunteer of 31 years old.

DETAILED DESCRIPTION

Figure 4A:
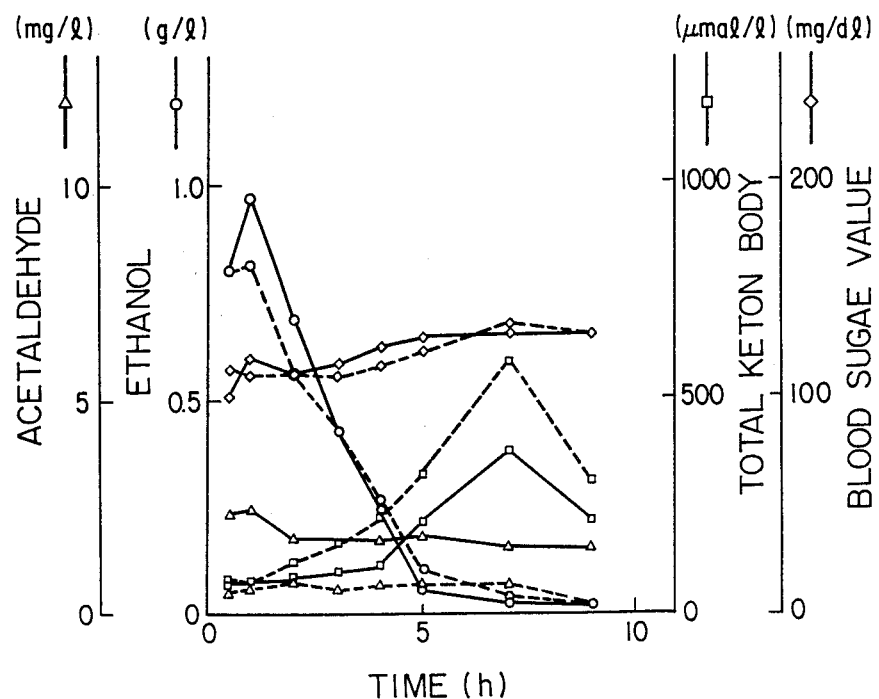
FIGS. 4a and 4b are graphical views illustrating the effect of phytic acid upon ethanol, acetaldehyde, total ketone body and a blood sugar value in the plasma of a rabbit when orally administered with ethanol in a dosage of 1 g/Kg.

In various preparations, phytates and their mixtures in a pH range of 6 to 8 may generally be selectively used depending upon the purposes of pharmaceutics, table luxuries, foodstuffs and so on, becuase of their strong acidity.

The phytates usable in the present invention may include innoxious metal salts as well as innoxious salts with organic salts, basic amino acids and organic ester residues such as those represented by potassium phytate, sodium phytate, ammonium phytate, arginine phytate, ornithine phytate, lysine phytate, histidine phytate, monoethanolamine phytate, diethanolamine phytate, triethanolamine phytate and glucamine phytate.

The number of moles of various bases required to regulate one mole of phytic acid to pH 6 to 8 is shown in Table 1.

TABLE 1

| Bases pH | 6.00 | 7.00 | 8.00 |
|---|---|---|---|
| NaOH | 7.34 | 8.21 | 8.94 |
| KOH | 7.34 | 8.23 | 8.94 |
| LiOH | 7.41 | 8.38 | 9.30 |
| $NH_4OH$ | 7.61 | 8.55 | 9.45 |
| $HOC_2HCH_2NH_2$ | 7.72 | 8.68 | 9.52 |
| $(HOCH_2CH_2)_2NH$ | 7.54 | 8.45 | 9.31 |
| $(HOCH_2CH_2)_3N$ | 7.20 | 8.53 | 12.1 |
| N-Methylglucamine | 7.62 | 8.49 | 9.25 |
| L-Arginine | 7.79 | 8.67 | 9.60 |
| L-Lysine | 8.01 | 8.98 | 10.0 |
| L-Histidine | 11.3 | — | — |

Phytic acid and its salt are so tasteless and odorless that their oral administration is easily achieved. Thus, the preventives or remedies provided by the present invention may be administrated by mixing with drinking water for humans and animals or sprinkling over or blending with dishes and feed in the form of powders or granules.

A dosage of 1 to 100 mg/kg/day of the preparations provided by the present invention may be suitable for humans, generally adults, although depending upon the conditions of patients and the type of preparations.

In sum, a detoxicating effect of the preparations in the present invention on drug poisoning and alcoholism is more easily obtained by oral administration, since they contain phytic acid and its salt as the main component.

Further, the preparations in or by the present invention may be administrated by way of an oral route, since, whether liquid or solid, phytic acid and its salt are found to be effective.

Still further, the preparations in or by the present invention may be applicable at need to the prevention of intoxication during driving, etc., in addition to the remedy of acute alcoholism and the prevention of crapulence.

Still further, the compositions of the preparations in the present invention are of safety so high that they are continuously usable and are effective for improvements in chronic alcoholism by their continued use or administration.

The present invention will now be explained in more detail with reference to the following non-restrictive examples.

EXAMPLE 1

Test Examples

1. Testing for the Deodorization of Alcoholic Breath

Alcohol (300 ml of sake) with 105 mg/ml of potassium phytate was orally administered to a first group of three healthy subjects with an empty stomach, who declared to be easily overcome by drink, whereas only an ill-smelling substance was applied to a second group of subjects to carry out breath organoleptic tests-with-time, the results of which were then declared by the subjects themselves and estimated by three impartial examiners.

The results were estimated to be positive, when two of the three examiners did so.

Testing Results

In the organoleptic tests by the impartial examiners, they judged that the second group of subjects had an alcoholic breath, three and six hours after the administration, whereas the first group of subjects had no alcoholic breath from the very early hour after the administration. Referring to the results declared by the subjects, the second group of subjects complained of acute poisoning symptoms such as nausea, rubescence, intoxication and auditive abnormality, whereas the first group of subjects did not complain of any abnormality whatsoever.

2. Alcoholometry Testing

After lunch, three male volunteers (26, 72 kg; 27, 56 kg; 31, 72 kg) were alcoholized by 300 ml of sake to measure the concentration of alcohol in breath with the lapse of time.

Two days later, the same subjects were alcoholized by sake, immediately followed by the administration of 105 mg/10 ml of potassium phytate (pH 7.0), for the measurement-with-time of the concentration of alcohol in breath.

Plotted in FIGS. 1 to 3 are the results, from which it was found that the concentration of alcohol in breath was reduced by the administration of phytic acid.

3. Testing by Panelists Fond of Alcohol

After drinking, the drinkable solution of Preparation Example 1 was dosed to three panelists fond of alcohol. On inquiry of their drinking habit one month later, all the panelists answered about the effect of the Preparation Examples that there was a decrease in the amount of drinking.

4. Effect on Improvements in the Drug Poisoning of Mice

A group of six mice were put under anesthesia by the abdominal administration of 80 mg/kg of hexobarbital, and were then abdominally administrated with 10 mg/kg of potassium phytate within 10 minutes for the comparison and investigation of the arousal time. As a result, it was found that there was a 30% or higher reduction in the arousal time.

5. Taste Testing

One hundred and eighty (180)-milliliter shots of sake and whisky-and-water containing 0.5 g (100 mg calculated as phytic acid) of the liquid preparation according to Preparation Example 4 were simultaneously provided to two 20-member panels to carry out taste testing for comparing both the shots in terms of whether taste and smell are good or bad. The results are set forth in the following table.

|  | Undistinguishable from Phytic Acid-Free Shots | Better than Phytic Acid-Free Shots | Bad |
| --- | --- | --- | --- |
| Taste | 14 | 6 | 0 |
| Smell | 18 | 2 | 0 |

From the above results, it has been found that the preparation according to the present invention tastes good, and is effective as a liquor additive.

6. Testing for the Estimation of Alcoholic Metabolism

The alcoholometry testing (2) revealed that when the amount of alcohol in breath was smaller when ingesting potassium phytate simultaneously with drinking then when not. The present inventors believed that this resulted from the process of metabolism, viz., oxidation of alcohol being accelerated by the ingestion of phytic acid.

Therefore, the metabolism of alcohol was estimated by determining the alcohol content in blood of a rabbit before and after the administration of phytic acid as well as acetaldehyde and ketone body, viz., the metalbolites of alcohol.

Procedures (a) Animal and Blood-Collecting Method

An amount of blood was collected from the aural veins of a Japanese white rabbit weighing about 3 Kg (available from Kitayama Rabbitry), and was added with 3 mg/ml of sodium citrate to separate plasma by Suresep (manufactured by Ono Pharmaceutical Co., Ltd.).

(b) Sodium Phytate

Sodium phytate (Nakarai Chemical Co., Ltd., Lot No. M7K7653) was dissolved in PBS, regulated to pH 7.2 with 6N HCl, and was then adjusted to an amount of 20 mg/ml. This was continuously administered to the abdominal cavity of the rabbit in a dosage of 20 mg per Kg of weight for 4 to 6 days.

(c) Alcohol

Fifteen or thirty (15 or 30) % of ethanol (guranteed reagent; manufactured by Wako Junyaku K. K.) diluted by distilled water were orally administered to the rabbit in a dosage of 1 g or 2 g of ethanol per Kg of weight by means of a probe.

(d) Measurement of the Concentration of Alcohol in Blood

The concentration of alcohol in blood was measured by F Kit Ethanol (Beringer-Mannheim Yamanouchi, Lot No. 613191).

(e) Measurement of the Concentration of Acetaldehyde in Blood

The concentration of acetaldehyde in blood was measured by F Kit Acetaldehyde (Berginer-Mannheim Yamanouchi, Lot No. 610683).

(f) Measurement of the Concentration of Ketone Body in Blood

The concentration of ketone body in blood was measured by Ketone Test (Sanwa Lot No. K015).

(g) Measurement of Blood Sugar Value

The blood sugar value was measured by Glucose B-Test Wako Lot No. PR020.

Conditions for the Administration of Phytic Acid and Alcohol

In order to have a thorough understanding of the effect of sodium phytate, it was administrated to the rabbit by way of an intraperitonal route ip.

Sodium phytate was administered to the rabbit in a dosage of 20 mg/Kg that was ten times as large as the dosage found to be effective in the test for the deodorization of rat's urine and in a continuous manner to clarify its effect.

The concentration of alcohol corresponding to the degree of intoxication of humans (slight to medium intoxication) could be reproduced in the rabbit (the concentration of alcohol in blood: 0.08 to 0.15%), and was administrated to the rabbit in a dosage of 1 g/Kg or 2 g/Kg.

Results (a) Administration of 1 g/Kg of Alcohol

After two rabbits (Rabbit 1 and 2) had been fasted for 24 hours, 1 g/Kg of alcohol was administered to the rabbits, and the concentrations of alcohol, acetaldehyde, ketone body and blood sugar in blood were measured with time. After the lapse of one week, sodium phytate was continuously administered to the same rabbits for four days, and they were fasted for further 24 hours from the final administration. Afterwards, alcohol was was likewise administrated to them and the above-mentioned concentrations were measured.

Figure 4B:
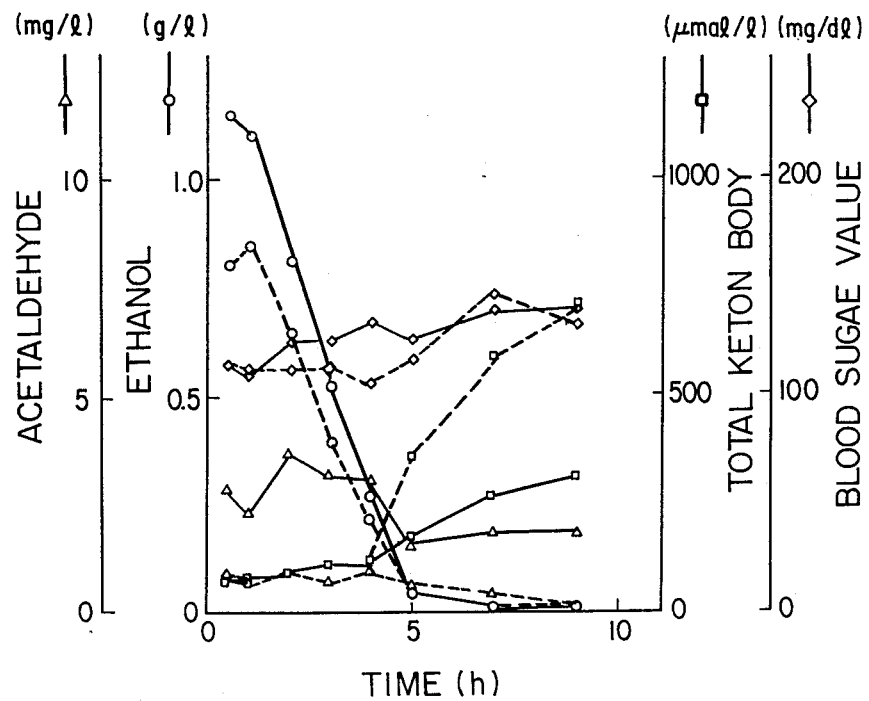

As shown in FIG. 4, it was revealed that the amounts of alcohol and acetaldehyde in blood were reduced by the administration of phytic acid. On the other hand, the amount of ketone body was approximately doubled by the administration of phytic acid. Blood sugar was temporarily reduced by the administration of alcohol, but was found to be not largely affected by the administration of phytic acid.

(b) Administration of 2 g/Kg of Alcohol

In Experiment (a), 1 g/Kg of alcohol did not give rise to the formation of acetaldehyde. Therefore, the dosage of alcohol to administrate to two rabbits (Rabbit 3 and 4) was doubled to 2 g/Kg. As was the case with Experiment (a), phytic acid was administered to the rabbits in a dosage of 20 mg/Kg for six days under the same conditions.

Figure 5A:
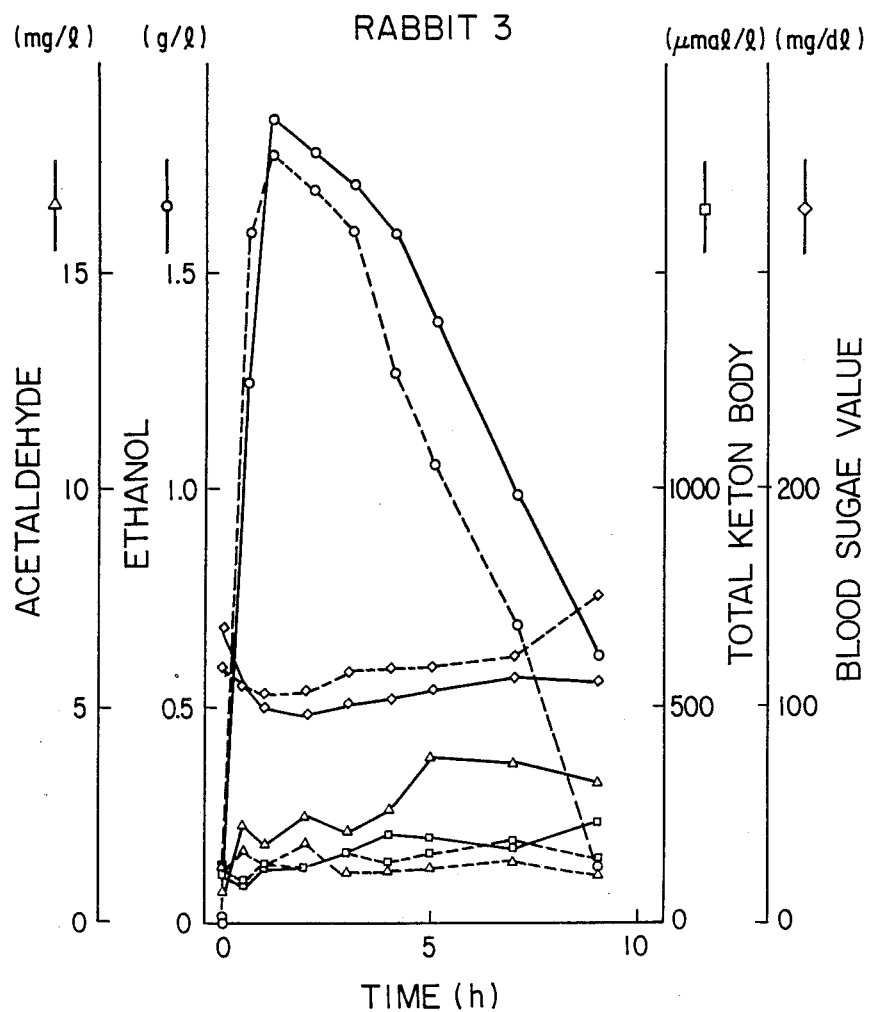
FIGS. 5a and 5b are graphical views illustrating the effect of phytic acid upon ethanol, acetaldehyde, total ketone body and a blood sugar value in the plasma of a rabbit when orally administered with ethanol in a dosage of 2 g/Kg.
Figure 5B:
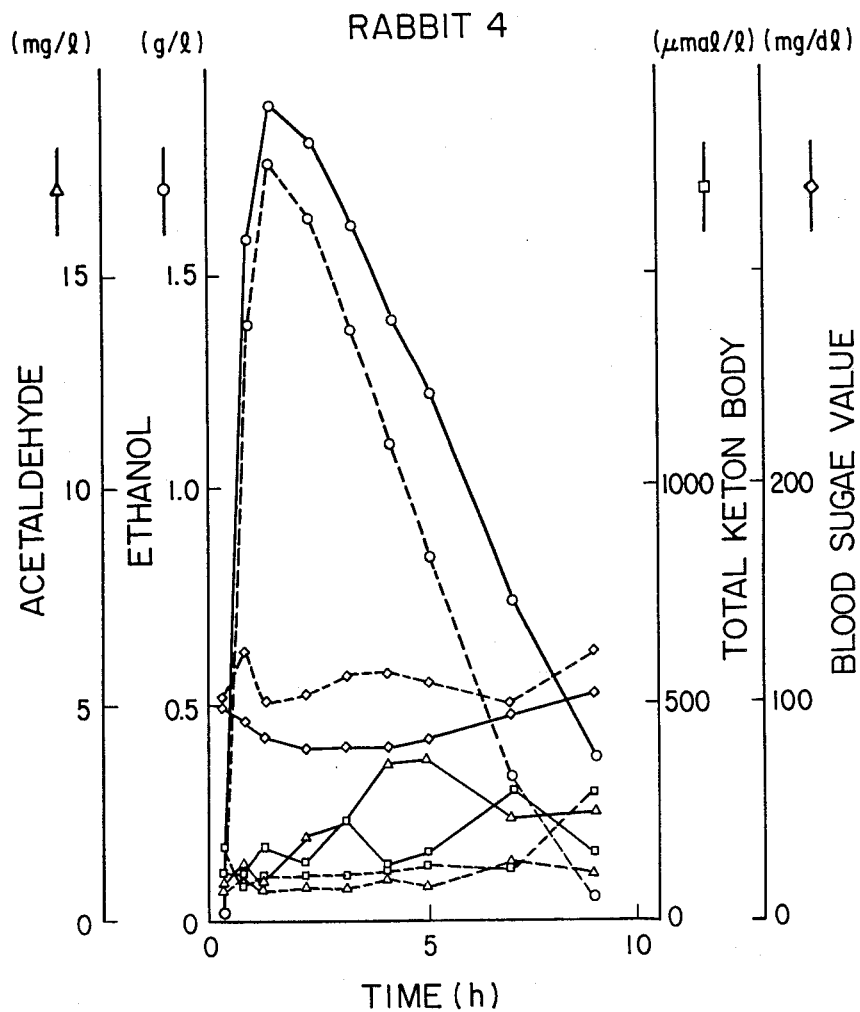

Changes in the amounts of the components in blood with and without the administration of phytic acid are illustrated in FIG. 5. As was the case with Experiment (a), it was ascertained that the amounts of alcohol and acetaldehyde in blood were reduced after the administration of phytic acid in comparison with the absence thereof. Any increase in the amount of ketone body was not found within the time during which blood was collected. However, the amount of ketone body would be likely to increase after alcohol disappeared from blood. It was also noted that slight increases or decreases in the blood sugar value were prevented by the administration of phytic acid.

Considerations

Because alcohol was orally administrated to the rabbits fasted for 24 hours, it is considered that alcohol was 100 percent absorbed from digestive tracts. The experimental results suggest that the metabolism of alcohol is accelerated in rabbits to which phytic acid is administrated. In addition, it was confirmed that highly toxic acealdehyde, that is, an intermediate metabolite of not only ethanol but also alcohol underwent remarkable decomposition. This indicates that the metabolic capability of the liver is improved, since the metabolism of alcohol mostly takes place in the liver.

It is appreciated that the formation of ketone body is further augmented due to the rapidty of the metabolism of alcohol. This is considered to reflect normal metabolic reactions.

As mentioned above, it has been noted that phytic acid acts upon the liver to augment the metabolic capability of alcohol. This suggests that phytic acid enhances the functions of not only cellular cytoplasms but also mitochondria.

EXAMPLE 2

Composition a

Twenty-nine (29) g of sodium hydroxide and a suitable amount of refined water are added to 660 g of phytic acid (as an anhydride) to obtain a liquid regulated to pH 6.

Composition b

Four hundred and twelve (412) g of potassium hydroxide and a suitable amount of refined water are added to 660 g of phytic acid (as an anhydride) to obtain a liquid regulated to pH 6.

Composition c

One hundred and seventy-seven (177) g of lithium hydroxide and a suitable amount of refined water are added to 660 g of phytic acid (as an anhydride) to obtain a liquid regulated to pH 6.

Composition d

Five hundred and eighty-one (581) g of ethanolamine and a suitable amount of refined water are added to 660 g of phytic acid (as an anhydride) to obtain a liquid regulated to pH 8.

Composition e

Nine hundred and seventy-nine (979) g of diethanolamine and a suitable amount of refined water are added to 660 g of phytic acid (as an anhydride) to obtain a liquid regulated to pH 8.

Composition f

One thousand eight hundred and five (1805) g of triethanolamine and a suitable amount of refined water are added to 660 g of phytic acid (as an anhydride) to obtain a liquid adjusted to pH 8.

Composition g

One thousand six hundred and fifty-seven (1657) g of N-methylglucamine and a suitable amount of refined water are added to 660 g of phytic acid (as an anhydride) to obtain a liquid adjusted to pH 7.

Composition h

One thousand five hundred and ten (1510) g of L-arginine and a suitable amount of refined water are added to 660 g of phytic acid (as an anhydride) to obtain a liquid adjusted to pH 7.

Composition i

One thousand seven hundred and fifty-three (1753) g of L-histidine and a suitable amount of refined water are added to 660 g of phytic acid (as an anhydride) to obtain a liquid adjusted to pH 6.

Composition j

One hundred and sixteen (116) g of sodium hydroxide, 478 g of potassium hydroxide, 6.08 g of potassium chloride (as a dihydrate), 157 g of disodium hydrogen phosphate (as an anhydride) and a suitable amount of refined water are added to 660 g of phytic acid (as an anhydride) to obtain a liquid adjusted to pH 9.

These compositions a to j may be powderized by crystallization or the addition of a vehicle.

These compositions a to j may also be formed into compositions in the form of liquids or powders, from which the preparations may be obtained.

EXAMPLE 3

The composition j obtained in Example 2 was formed into a composition, from which various preparations were obtained.

Composition A for Preparations

Lactose is added to the composition j (containing 200 mg of phytic acid) to obtain a total of 1000 mg of a composition.

Composition B for Preparations

Lactose is added to the composition j (containing 100 mg of phytic acid) to obtain a total of 1000 mg of a composition.

Composition C for Preparations

Refined water is added to the composition j (containing 100 mg of phytic acid) to obtain a total of 1000 mg of a composition.

Composition D

Light silicic anhydride is added to the composition j (containing 200 mg of phytic acid), followed by drying, which gives a total of 1000 mg of a composition.

PRODUCTION EXAMPLES OF PREPARATIONS

Production Example 1 (Erixir)

Composition C: 100 g (10 g calculated as phytic acid)
Compound orange extract: 24 ml
Ethanol: 400 ml
Glycerine: 400 ml
Refined water: Total: 1000 ml Predetermined amounts of the aforesaid components are uniformly mixed together to obtain a colorless and clear erixir preparation. A five-milliliter dosage of this erixir preparation contains 50 mg of phytic acid.

Production Example 2 (Capsule)

Composition A: 200 mg (40 mg calculated as phytic acid)
Lactose: 20 mg
Corn starch: 38 mg
Magnesium stearate: 2 mg Predetermined amounts of the aforesaid components are uniformly mixed together and packed in No. 2 capsules. One such capsule contains 40 mg of phytic acid.

Production Example 3 (Granule)

Composition A: 600 mg (120 mg calculated as phytic acid)
Lactose: 140 mg
Corn starch: 250 mg
Hydroxypropylcellulose: 10 mg Predetermined amounts of the aforesaid components are uniformly mixed together, and the mixture is then wet-granulated with water and ethanol into granules. One hundred and twenty (120) mg of phytic acid are contained in an one-gram dosage of such granules.

Production Example 4 (Powder)

The composition A is divided and heat-sealed in aluminium to obtain wrappers each of 1.5 g.

Production Example 5 (Tablet)

Composition A: 100 mg (20 mg calculated as phytic acid)
Corn starch: 19 mg
Crystalline cellulose: 30 mg
Magnesium stearate: 1 mg Predetermined amounts of the aforesaid components are uniformly mixed together, and the mixture is then compressed into tablets each of 7 mm in diameter and 150 mg in weight. One such tablet contains 20 mg of phytic acid.

Production Example 6 (Syrup)

Composition C: 50 g (5 g calculated as phytic acid)
White sugar: 300 g
D-sorbitol (70%): 250 g
Methyl p-oxybenzoate: 0.3 g
Propyl p-oxybenzoate: 0.15 g
Sodium citrate: 10 g
Perfume: 1.5 g
Refined water: Total: 1000 ml Predetermined amounts of the aforesaid components are dissolved and mixed together into a colorless and clear syrup. One hundred (100) mg of phytic acid is contained in a twenty-milliliter dosage of this syrup.

Production Example 7 (Dry syrup)

Composition B: 100 mg (10 mg calculated as phytic acid)
Sodium citrate: 2.4 mg
Citric anhydride: 2.2 mg
Tragacanth powders: 2.7 g
White sugar: suitable amount
Hydroxypropylcellulose: 3.0 mg
Perfume: slight amount Predetermined amounts of the aforesaid components are uniformly mixed together, and are then wet-granulated with water and ethanol into a dry syrup. An one (1)-gram dosage of this syrup contains 10 mg of phytic acid.

Production Example 8 (Troche)

Composition A: 100 mg (20 mg calculated as phytic acid)

White sugar: 870 mg
Lactose: 20 mg
Magnesium stearate: 10 mg

Of the aforesaid components the composition A and white sugar are uniformly mixed together in the respective amounts of 100 g and 870 g, and are then wet-granulated with water and ethanol, followed by drying at a temperature of lower than 35° C. Added to the dried product are 20 g of lactose and 10 g of magnesium stearate to obtain troches each of 15 mm in diameter and 1 g in weight. One such troche contains 20 mg of phytic acid.

Production Example 9 (Candy)

Composition B: 100 mg (10 mg calculated as phytic acid)
White sugar: 2400 mg
Starch syrup: 1500 mg
Perfume: slight amount Of the aforesaid components, 240 g of white sugar and 150 g of starch syrup are mixed with 100 g of refined water. After melting by heating, the mixture is sieved out for the removal of foreign matters. The resulting liquid is concentrated under pressure with the application of heat for dehydration to prepare a starch syrup dough having a moisture content of 2 to 3% at 130° to 150° C. Added to this dough are 10 g of the composition B and a slight amount of perfume, and the product is molded to obtain candies each of 4 g in weight. Each candy contains 10 mg of phytic acid.

Production Example 10 (Limonada)

Composition C: 3 g (300 mg calculated as phytic acid)
Syrup: 2.5 ml
Refined water: Total: 30 ml Predetermined amounts of the aforesaid components are uniformly mixed together into limonadas. A thirty (30)-milliliter dosage of such limonadas contains 300 mg of phytic acid.

Production Example 11 (Granule)

Composition D: 500 mg (100 mg calculated as phytic acid)
Garlic powders: 750 mg
Lactose: suitable amount Predetermined amounts of the aforesaid components are uniformly mixed together, and are then wet-granulated with water and ethanol into granules. One hundred (100) mg of phytic acid is contained in an 1.5-gram dosage of such granules.

Production Example 12 (Drinkable Solution)

Composition C: 1 g (100 mg calculated as phytic acid)
Mel: 0.5 g
White sugar: 2.0 g
Citric acid: suitable amount
Sodium citrate: suitable amount
Peppermint: slight amount
Refined water: suitable amount Predetermined amounts of the aforesaid components were uniformly mixed together into a colorless and clear internal liquid preparation. A thirty (30)-milliliter dosage of this liquid preparation contains 100 mg of phytic acid.

Production Example 13 (Garlic Flavoring)

Composition D: 0.285 g (0.1 g calculated as phytic acid)
Avisel: 0.18 g
Garlic powders: 0.75 g
Light silicic anhydride: 0.256 g
Corn starch: suitable amounts Predetermined amounts of the aforesaid components are granulated by a conventional method.

Stability Testing

The preparations according to Production Examples 1 to 10 were subjected to stability testing to measure the amount of residual phytic acid. The results are set forth in Table 2.

TABLE 2

Amounts of Residual Phytic Acid in the Stability Testing of the Preparations According to the Production Examples (% with respect to the specified contents)

| Samples | Storage Vessels | At the beginning of Storage | After 3 weeks at 60° C. |
| --- | --- | --- | --- |
| P.Ex.1A* | Glass Bottle | 100.5 | 101.2 |
| P.Ex.2B* | PTP | 101.4 | 99.4 |
| P.Ex.3C* | Aluminium Wrapper | 100.1 | 100.0 |
| P.Ex.4D* | Aluminium Wrapper | 100.9 | 102.1 |
| P.Ex.5E* | PTP | 99.2 | 99.8 |
| P.Ex.6F* | Glass Bottle | 102.1 | 100.3 |
| P.Ex.7G* | Aluminium Wrapper | 100.6 | 100.1 |
| P.Ex.8H* | Aluminium SP | 99.7 | 100.5 |
| P.Ex.9I* | Aluminium Bag | 99.9 | 99.2 |
| P.Ex.10J* | Glass Bottle | 102.1 | 100.9 |
| P.Ex.11K* | Aluminium Wrapper | 100.3 | 100.1 |
| P.Ex.12L* | Glass Bottle | 100.1 | 99.8 |

A*: Erixir, B*: Capsul, C*: Granule, D*: Powder, E*: Tablet, F*: Syrup, G*: Dry Syrup, H*: Troche, I*: Candy, J*: Limonada, K*: Granule, L*: Drinkable Solution.

What is claimed is:

1. A method for preventing or treating alcohol poisoning which comprises administering to an animal in need of such treatment an effective amount of phytic acid or a pharmaceutically acceptable salt thereof.

2. A method according to claim 1, wherein the salt is an alkali metal or an ammonium salt.

3. A method according to claim 1, wherein the salt is a salt with an amino acid.

4. A method according to claim 1, wherein the phytic acid or salt thereof is administered orally.

5. A method according to claim 4, wherein the amount of the orally administered phytic acid or salt thereof is 1 to 100 mg/kg/day.

* * * * *